US012611163B2

(12) United States Patent
Takemoto

(10) Patent No.: US 12,611,163 B2
(45) Date of Patent: Apr. 28, 2026

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventor: Kosei Takemoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/818,246

(22) Filed: Aug. 28, 2024

(65) Prior Publication Data

US 2024/0415486 A1      Dec. 19, 2024

Related U.S. Application Data

(63) Continuation of application No. PCT/JP2023/005619, filed on Feb. 17, 2023.

(30) Foreign Application Priority Data

Mar. 3, 2022      (JP) ................................. 2022-032503

(51) Int. Cl.
*A61B 8/08*           (2006.01)
*A61B 8/00*           (2006.01)
(52) U.S. Cl.
CPC ............ *A61B 8/0825* (2013.01); *A61B 8/406* (2013.01); *A61B 8/54* (2013.01)
(58) Field of Classification Search
CPC ......... A61B 8/0825; A61B 8/406; A61B 8/54; A61B 8/085; A61B 8/463; A61B 8/467; A61B 8/468; A61B 8/00; A61B 8/5292
See application file for complete search history.

(56) References Cited

U.S. PATENT DOCUMENTS

| | | | |
|---|---|---|---|
| 2005/0240882 A1 | 10/2005 | Morita et al. | |
| 2010/0185571 A1 | 7/2010 | Sawada | |
| 2015/0342563 A1* | 12/2015 | Takahashi | A61B 8/465 |
| | | | 600/440 |
| 2017/0100098 A1* | 4/2017 | Urabe | A61B 8/085 |

(Continued)

FOREIGN PATENT DOCUMENTS

| | | |
|---|---|---|
| JP | 2010-165305 A | 7/2010 |
| JP | 2012-135428 A | 7/2012 |
| JP | 2015-112123 A | 6/2015 |

(Continued)

OTHER PUBLICATIONS

International Search Report issued in PCT/JP2023/005619; mailed Mar. 28, 2023.

(Continued)

*Primary Examiner* — Kaitlyn E Sebastian
(74) *Attorney, Agent, or Firm* — Studebaker Brackett PLLC

(57) ABSTRACT

An ultrasound diagnostic apparatus for an examiner to perform an ultrasound examination on a breast of a subject includes: a voice acquisition sensor (3) that acquires a voice during the ultrasound examination; a voice analysis unit (24) that estimates an examination position of the subject by analyzing the voice acquired by the voice acquisition sensor (3); and a body mark setting unit (25) that selects and sets one of left and right breast body marks based on the examination position of the subject estimated by the voice analysis unit (24).

20 Claims, 6 Drawing Sheets

(56)                    References Cited

U.S. PATENT DOCUMENTS

2021/0315540 A1    10/2021   Ooi et al.

FOREIGN PATENT DOCUMENTS

| JP | 2015104464 A | * | 6/2015 |
| JP | 2015-226607 A | | 12/2015 |
| JP | 2021-166574 A | | 10/2021 |

OTHER PUBLICATIONS

International Preliminary Report on Patentability (Chapter I) and Written Opinion of the International Searching Authority issued in PCT/JP2023/005619; issued Aug. 30, 2024.

* cited by examiner

FIG. 7

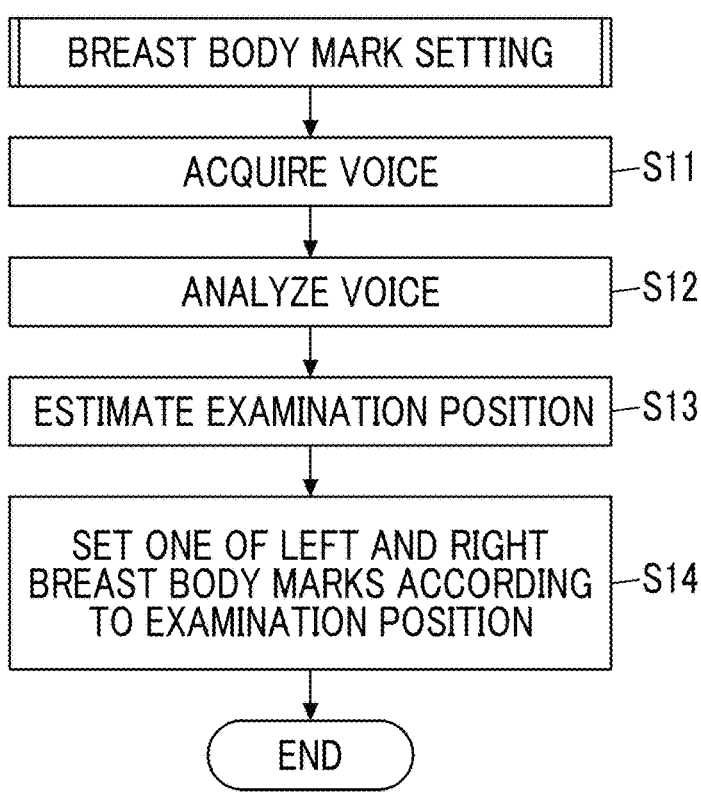

```
BREAST BODY MARK SETTING

↓

ACQUIRE VOICE                        —S11

↓

ANALYZE VOICE                        —S12

↓

ESTIMATE EXAMINATION POSITION        —S13

↓

SET ONE OF LEFT AND RIGHT
BREAST BODY MARKS ACCORDING          —S14
TO EXAMINATION POSITION

↓

END
```

FIG. 8

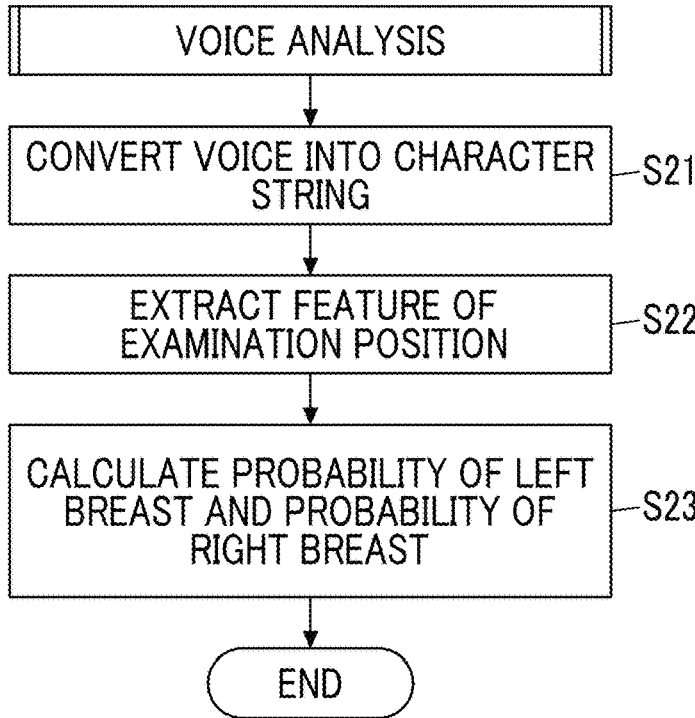

```
VOICE ANALYSIS

↓

CONVERT VOICE INTO CHARACTER         —S21
STRING

↓

EXTRACT FEATURE OF                   —S22
EXAMINATION POSITION

↓

CALCULATE PROBABILITY OF LEFT
BREAST AND PROBABILITY OF            —S23
RIGHT BREAST

↓

END
```

ULTRASOUND DIAGNOSTIC APPARATUS AND CONTROL METHOD OF ULTRASOUND DIAGNOSTIC APPARATUS

CROSS-REFERENCE TO RELATED APPLICATIONS

This application is a Continuation of PCT International Application No. PCT/JP2023/005619 filed on Feb. 17, 2023, which claims priority under 35 U.S.C. § 119(a) to Japanese Patent Application No. 2022-032503 filed on Mar. 3, 2022. The above applications are hereby expressly incorporated by reference, in their entirety, into the present application.

BACKGROUND OF THE INVENTION

1. Field of the Invention

The present invention relates to an ultrasound diagnostic apparatus that examines a breast of a subject and a control method of the ultrasound diagnostic apparatus.

2. Description of the Related Art

Conventionally, an examination of breasts of a subject has been performed by capturing an ultrasound image using a so-called ultrasound diagnostic apparatus. In the examination of the breasts of the subject, in order to easily determine which of left and right breasts of the subject is captured in the captured ultrasound image, a so-called body mark indicating the left breast or a body mark indicating the right breast is often set to correspond to the ultrasound image. In addition, such a body mark is often set manually by an examiner.

Since it is usually difficult to determine which of the left and right breasts of the subject is captured in the ultrasound image by confirming the ultrasound image, it is difficult to confirm the ultrasound image after the examination to correctly re-set the body mark, for example, in a case where the examiner incorrectly sets a body mark corresponding to the breast on a side opposite to the actual breast of the subject. In response, as disclosed in, for example, JP2021-166574A, JP2015-226607A, and JP2012-135428A, a technology for automatically setting the body mark has been developed. JP2021-166574A discloses that position information of an ultrasound probe is acquired by using a magnetic sensor or the like, and a body mark indicating either a left or right breast is automatically set based on the acquired position information. JP2015-226607A discloses that a body mark corresponding to an examination position of a subject is set based on an optical image of the subject. JP2012-135428A discloses that a body mark indicating either a left or right breast is set in association with an ultrasound image based on information stored in an X-ray image captured in advance.

SUMMARY OF THE INVENTION

However, according to the technologies of JP2021-166574A, JP2015-226607A, and JP2012-135428A, there are cases where, due to a need to prepare an expensive and complicated apparatus, the apparatus cannot be easily introduced.

The present invention has been made in order to solve such a conventional problem, and an object of the present invention is to provide an ultrasound diagnostic apparatus and a control method of an ultrasound diagnostic apparatus capable of accurately setting a body mark of a breast while having an inexpensive and simple apparatus configuration.

The above-described object can be achieved by the following configuration.

[1] An ultrasound diagnostic apparatus for an examiner to perform an ultrasound examination on a breast of a subject, the ultrasound diagnostic apparatus comprising:
a voice acquisition sensor that acquires a voice during the ultrasound examination;
a voice analysis unit that estimates an examination position of the subject by analyzing the voice acquired by the voice acquisition sensor; and
a body mark setting unit that selects and sets one of left and right breast body marks based on the examination position of the subject estimated by the voice analysis unit.

[2] The ultrasound diagnostic apparatus according to [1], in which the voice analysis unit detects a series of operation transitions of the ultrasound examination by analyzing the voice acquired by the voice acquisition sensor and estimates the examination position based on the detected series of operation transitions.

[3] The ultrasound diagnostic apparatus according to [1] or [2], further comprising:
an input device that accepts input of any of the left and right breast body marks through an input operation by the examiner prior to the ultrasound examination.

[4] The ultrasound diagnostic apparatus according to [3], further comprising:
a notification unit that issues a notification to the examiner,
in which, in a case where the breast body mark selected by the body mark setting unit is different from the breast body mark input through the input device, the notification unit issues a notification of an error.

[5] The ultrasound diagnostic apparatus according to [3], in which, in a case where the breast body mark selected by the body mark setting unit is different from the breast body mark input through the input device, the body mark setting unit sets the breast body mark selected based on the examination position of the subject estimated by the voice analysis unit, instead of the breast body mark input through the input device.

[6] The ultrasound diagnostic apparatus according to any one of [1] to [5], in which the voice analysis unit converts the voice acquired by the voice acquisition sensor into a character string, extracts a feature related to the examination position from the converted character string, calculates a first probability that the examination position is a left breast and a second probability that the examination position is a right breast, and estimates the examination position based on the first probability and the second probability.

[7] The ultrasound diagnostic apparatus according to [6], in which the voice analysis unit calculates, in a case where there is a specific examination sequence for an ultrasound examination of the left and right breasts, the first probability and the second probability based on respective prior probabilities corresponding to the specific examination sequence.

[8] The ultrasound diagnostic apparatus according to [6] or [7], in which the voice analysis unit increases, in a case where voice data including dialogue between the subject and the examiner following a predetermined guideline is acquired by the voice acquisition sensor, a weight of the calculation of the first probability or the second probability based on the voice data.

[9] The ultrasound diagnostic apparatus according to any one of [1] to [8], further comprising:

an ultrasound probe;

an image acquisition unit that acquires an ultrasound image in the breast of the subject by performing transmission and reception of an ultrasound beam using the ultrasound probe; and a monitor that displays the ultrasound image.

[10] The ultrasound diagnostic apparatus according to [9], in which the breast body mark selected by the body mark setting unit is displayed on the monitor together with the ultrasound image.

[11] A control method of an ultrasound diagnostic apparatus for an examiner to perform an ultrasound examination on a breast of a subject, the control method comprising:

acquiring a voice during the ultrasound examination;

estimating an examination position of the subject by analyzing the acquired voice; and selecting and setting one of left and right breast body marks based on the estimated examination position of the subject.

According to the present invention, there is provided an ultrasound diagnostic apparatus for an examiner to perform an ultrasound examination on a breast of a subject, the ultrasound diagnostic apparatus comprising: a voice acquisition sensor that acquires a voice during the ultrasound examination; a voice analysis unit that estimates an examination position of the subject by analyzing the voice acquired by the voice acquisition sensor; and a body mark setting unit that selects and sets one of left and right breast body marks based on the examination position of the subject estimated by the voice analysis unit. Therefore, it is possible to accurately set the body mark of the breast while having an inexpensive and simple apparatus configuration.

BRIEF DESCRIPTION OF THE DRAWINGS

FIG. 7 is a flowchart showing an operation of breast body mark setting in the embodiment of the present invention.

FIG. 8 is a flowchart showing an operation of voice analysis in the embodiment of the present invention.

DESCRIPTION OF THE PREFERRED EMBODIMENTS

Hereinafter, embodiments of the present invention will be described with reference to the accompanying drawings.

Although descriptions of configuration requirements to be described below are made based on a representative embodiment of the present invention, the present invention is not limited to such an embodiment.

In the present specification, a numerical range represented by "to" means a range including numerical values described before and after "to" as a lower limit value and an upper limit value.

In the present specification, "same" and "identical" include error ranges generally allowed in the technical field.

Embodiment

Figure 1:
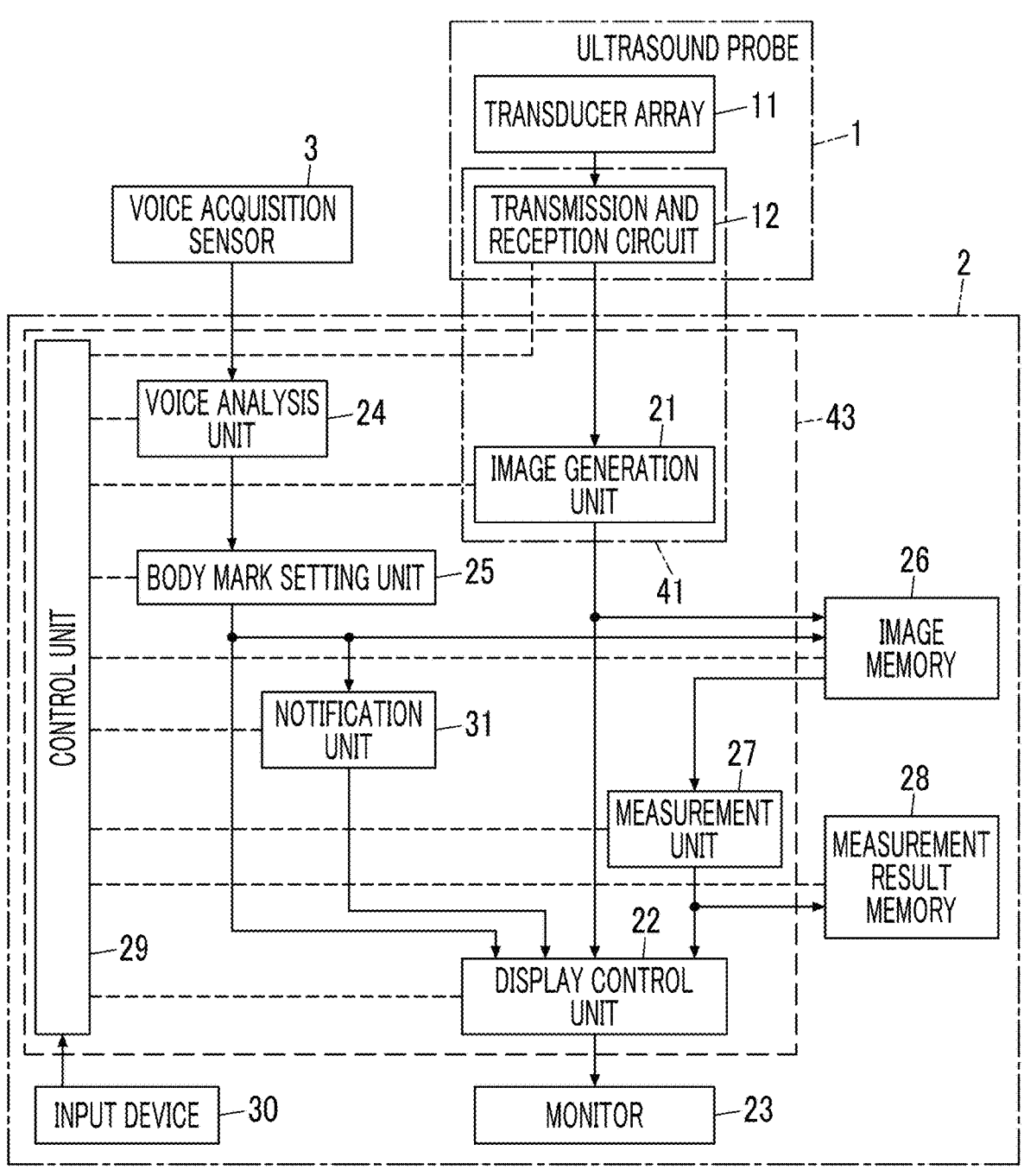
FIG. 1 is a block diagram showing a configuration of an ultrasound diagnostic apparatus according to an embodiment of the present invention.

FIG. 1 shows a configuration of an ultrasound diagnostic apparatus according to an embodiment of the present invention. The ultrasound diagnostic apparatus comprises an ultrasound probe 1, an apparatus body 2 connected to the ultrasound probe 1, and a voice acquisition sensor 3 connected to the apparatus body 2.

The ultrasound probe 1 includes a transducer array 11. A transmission and reception circuit 12 is connected to the transducer array 11.

The apparatus body 2 includes an image generation unit 21 connected to the transmission and reception circuit 12 of the ultrasound probe 1. A display control unit 22 and a monitor 23 are sequentially connected to the image generation unit 21. In addition, the apparatus body 2 includes a voice analysis unit 24 connected to the voice acquisition sensor 3. A body mark setting unit 25 is connected to the voice analysis unit 24. Further, an image memory 26 and a notification unit 31 are connected to the image generation unit 21 and the body mark setting unit 25. Additionally, a measurement unit 27 is connected to the image memory 26. Further, a measurement result memory 28 and the display control unit 22 are connected to the measurement unit 27. Moreover, the notification unit 31 is connected to the display control unit 22.

In addition, a control unit 29 is connected to the transmission and reception circuit 12, the image generation unit 21, the display control unit 22, the voice analysis unit 24, the body mark setting unit 25, the image memory 26, the measurement unit 27, the measurement result memory 28, and the notification unit 31. Further, an input device 30 is connected to the body mark setting unit 25 and the control unit 29.

In addition, the transmission and reception circuit 12 of the ultrasound probe 1 and the image generation unit 21 of the apparatus body 2 constitute an image acquisition unit 41. Further, the image generation unit 21, the display control unit 22, the voice analysis unit 24, the body mark setting unit 25, the measurement unit 27, the control unit 29, and the notification unit 31 of the apparatus body 2 constitute a processor 43 for the apparatus body 2.

The transducer array 11 of the ultrasound probe 1 includes a plurality of ultrasound transducers arranged one-dimensionally or two-dimensionally. These ultrasound transducers each transmit an ultrasound wave in accordance with a drive signal to be supplied from the transmission and reception circuit 12, receive an ultrasound echo from a subject, and output a signal based on the ultrasound echo. For example, each ultrasound transducer is composed of a piezoelectric body and electrodes formed at both ends of the piezoelectric body. The piezoelectric body consists of a piezoelectric ceramic represented by lead zirconate titanate (PZT), a polymer piezoelectric element represented by poly vinylidene di fluoride (PVDF), a piezoelectric single crystal represented by lead magnesium niobate-lead titanate (PMN-PT), or the like.

Figures 2, 3:
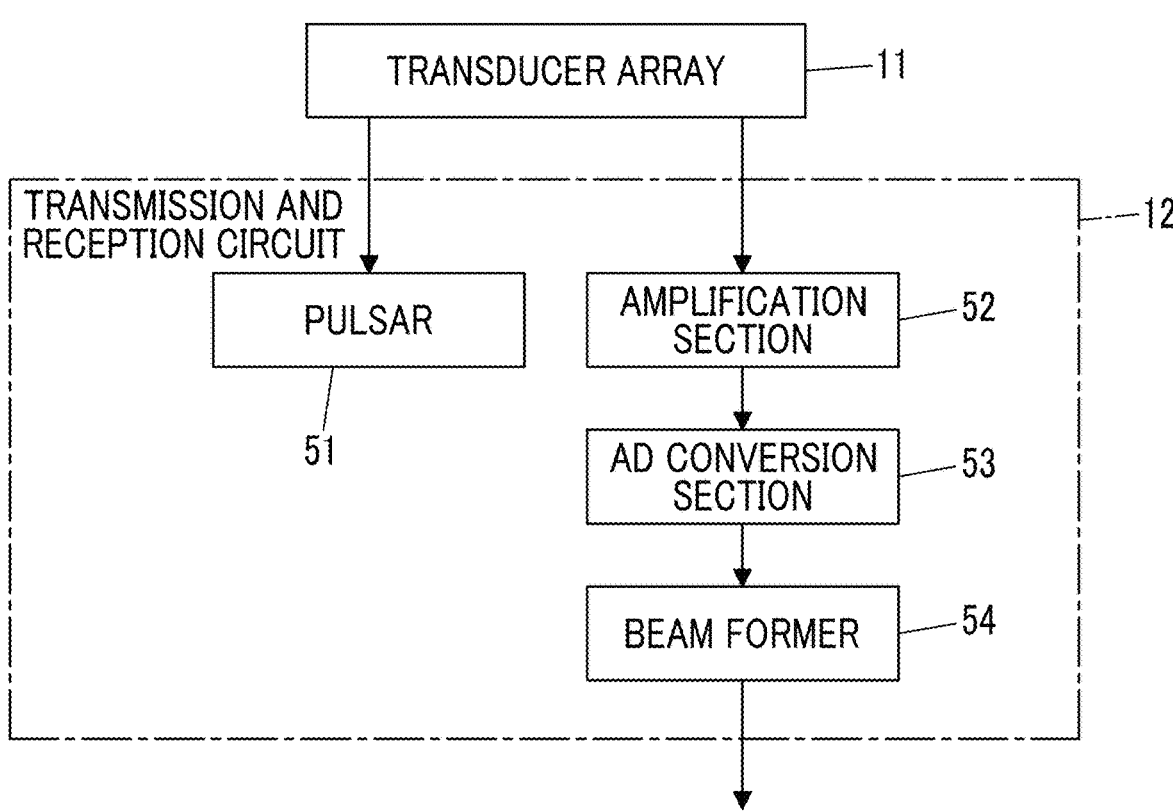
FIG. 2 is a block diagram showing a configuration of a transmission and reception circuit in the embodiment of the present invention.
FIG. 3 is a block diagram showing a configuration of an image generation unit in the embodiment of the present invention.

The transmission and reception circuit 12, under the control of the control unit 29, transmits the ultrasound wave from the transducer array 11 and generates a sound ray signal based on a reception signal acquired by the transducer array 11. The transmission and reception circuit 12 includes a pulsar 51 that is connected to the transducer array 11, and an amplification section 52, an analog-to-digital (AD) conversion section 53, and a beam former 54 that are sequentially connected in series from the transducer array 11, as shown in FIG. 2.

The pulsar 51 includes, for example, a plurality of pulse generators, and adjusts an amount of delay of each of drive signals and supplies the drive signals to the plurality of ultrasound transducers such that ultrasound waves transmitted from the plurality of ultrasound transducers of the transducer array 11 form an ultrasound beam, based on a transmission delay pattern selected according to a control signal from the control unit 29. In this manner, in a case where a pulsed or continuous wave-like voltage is applied to the electrodes of the ultrasound transducer of the transducer array 11, the piezoelectric body expands and contracts to generate a pulsed or continuous wave-like ultrasound wave from each of the ultrasound transducers, thereby forming an ultrasound beam from the combined wave of these ultrasound waves.

The transmitted ultrasound beam is reflected in, for example, a target such as a site of the subject and propagates toward the transducer array 11 of the ultrasound probe 1. The ultrasound echo that propagates toward the transducer array 11 in this manner is received by each of the ultrasound transducers that constitute the transducer array 11. In this case, each of the ultrasound transducers that constitute the transducer array 11 receives the propagating ultrasound echo to expand and contract to generate a reception signal which is an electrical signal, thereby outputting these reception signals to the amplification section 52.

The amplification section 52 amplifies the signal input from each of the ultrasound transducers that constitute the transducer array 11 and transmits the amplified signal to the AD conversion section 53. The AD conversion section 53 converts the signal transmitted from the amplification section 52 into digital reception data. The beam former 54 performs so-called reception focus processing by applying and adding a delay to each reception data received from the AD conversion section 53. Through the reception focus processing, the sound ray signal in which each reception data converted by the AD conversion section 53 is phase-added and a focus of the ultrasound echo is narrowed down is acquired.

As shown in FIG. 3, the image generation unit 21 has a configuration in which a signal processing section 55, a digital scan converter (DSC) 56, and an image processing section 57 are sequentially connected in series.

The signal processing section 55 generates a B-mode image signal, which is tomographic image information regarding tissues inside the subject, by performing, on the sound ray signal received from the transmission and reception circuit 12, envelope detection processing after performing correction of attenuation due to a distance according to a depth of a reflection position of the ultrasound wave using a sound velocity value set by the control unit 29.

The DSC 56 converts (raster-converts) the B-mode image signal generated by the signal processing section 55 into an image signal following a normal television signal scanning method.

The image processing section 57 performs various types of necessary image processing such as gradation processing on the B-mode image signal to be input from the DSC 56, and then sends the B-mode image signal to the display control unit 22 and the image memory 26. Hereinafter, the B-mode image signal that has been subjected to the image processing by the image processing section 57 will be referred to as an ultrasound image.

The display control unit 22, under the control of the control unit 29, performs predetermined processing on the ultrasound image or the like generated by the image generation unit 21 and displays the ultrasound image or the like on the monitor 23.

The monitor 23 performs various types of display under the control of the display control unit 22. Examples of the monitor 23 include a display device such as a liquid crystal display (LCD) or an organic electroluminescence (EL) display.

The voice acquisition sensor 3 includes a microphone and acquires a voice during an ultrasound examination as an electric signal. The voice during the ultrasound examination indicates a voice including a conversation between the examiner and the subject during the ultrasound examination. The voice acquisition sensor 3 sends information on the acquired voice to the voice analysis unit 24.

The voice analysis unit 24 estimates an examination position of the subject by the examiner by analyzing the voice acquired by the voice acquisition sensor 3. Here, the examination position refers to a position where the ultrasound probe 1 is in contact with a body surface of the subject in the ultrasound examination of the subject. In this case, for example, the voice analysis unit 24 can convert the voice acquired by the voice acquisition sensor 3 into a character string, extract a feature related to the examination position from the converted character string, and calculate a first probability that the examination position is the left breast of the subject and a second probability that the examination position is the right breast, thereby estimating the examination position based on the calculated first probability and second probability.

The voice analysis unit 24 can perform noise removal, distortion correction of the voice, and the like by performing so-called cepstrum analysis or the like with respect to the information representing the voice before converting the voice into the character string.

As a method for the voice analysis unit 24 to convert the voice into the character string, for example, known statistical methods such as a method described in US2002/0059069A or a method as described in "Frederick Jelinek (1998), "Statistical Methods for Speech Recognition", MIT Press, ISBN 0-262-10066-5" can be used. In a case where such a statistical method is used, for example, by using a so-called Bayes' theorem, probabilities of a plurality of candidates of the character string included in the voice acquired by the voice acquisition sensor 3 are calculated, and a most probable character string, among the these candidates of the character string, is picked out by taking into account the likelihood of the character string based on a language model, thereby enabling the conversion of the voice into the character string.

In a case where the voice analysis unit 24 calculates the candidates of the character string from the voice, for example, the voice analysis unit 24 analyzes a frequency component, a time change, and the like of sound waves in the voice, cuts out a feature amount for each sound from a waveform of the voice, and performs so-called pattern matching on the extracted feature amount, thereby specifying a phoneme corresponding to the feature amount. As a method of the pattern matching, for example, known algorithms such as a Gaussian mixture model-hidden Markov model or a deep neural network-hidden Markov model can be used.

Additionally, the voice analysis unit 24 stores in advance, for example, dictionary data including a plurality of words and can construct words from the phonemes by performing pattern matching between the specified phonemes and the plurality of words included in the dictionary data. In this case, the voice analysis unit 24 can construct the words by using, for example, a language model such as an N-gram or a recurrent neural network.

In addition, the voice analysis unit 24 stores in advance a plurality of character strings related to the examination of the right breast and a plurality of character strings related to the examination of the left breast, and extracts a feature related to the examination position, consisting of the character strings related to the examination of either the right or left breast, by comparing these character strings stored in advance and the character strings obtained by converting the voice with each other through pattern matching or the like. Examples of the character string related to the examination of the left breast include "left", "left breast", "left arm", and the like. Examples of the character string related to the examination of the right breast include "right", "right breast", "right arm", and the like.

the certain probability value from the prior probability for the second probability. As a result, the voice analysis unit 24 can calculate, for example, the first probability as 65% and the second probability as 35%.

The voice analysis unit 24 has a predetermined probability threshold value, and can specify the left breast as the examination position in a case where the first probability is equal to or greater than the probability threshold value and specify the right breast as the examination position in a case where the second probability is equal to or greater than the probability threshold value.

In addition, the voice analysis unit 24 can also detect a series of operation transitions of the ultrasound examination by analyzing the voice and estimate the examination position based on the detected series of operation transitions. In this case, for example, the voice analysis unit 24 can calculate the first probability and the second probability by storing in advance a plurality of examination contents, such as "examination start", "left breast examination in progress", "right breast examination in progress", "examination switching from the left breast to the right breast", "examination switching from the right breast to the left breast", and "examination end", and calculating the probabilities that the examination contents are currently being performed based on a specific character string included in a sentence specified from the voice.

In this case, the voice analysis unit 24 extracts, for example, in a case where sentences such as "start the examination", "start from the left breast", "start the examination of the right breast now", "raise the right hand", and "end the examination" are specified from the voice, as shown in Table 1, specific character strings such as "examination", "breast", "left", "right", "start", "raise hand", and "end" from among the sentences. Here, in Table 1, "1" represents that the character string is extracted from the specified sentence, and "0" represents that the character string is not extracted from the specified sentence.

TABLE 1

|  | Examination | Breast | Left | Right | Start | Raise hand | . . . | End |
|---|---|---|---|---|---|---|---|---|
| Start examination | 1 | 0 | 0 | 0 | 1 | 0 |  | 0 |
| Start from left breast | 0 | 1 | 1 | 0 | 0 | 0 |  | 0 |
| Start examination of right breast now | 1 | 1 | 0 | 1 | 1 | 0 |  | 0 |
| Raise right hand | 0 | 0 | 0 | 1 | 0 | 1 |  | 0 |
| . . . |  |  |  |  |  |  |  |  |
| End examination | 1 | 0 | 0 | 0 | 0 | 0 |  | 1 |

Further, the voice analysis unit 24 has an initial value (a prior probability for the first probability) of a first probability that the examination position is the left breast and an initial value (a prior probability for the second probability) of a second probability that the examination position is the right breast and performs weighting on the first probability and the second probability based on the number of extracted character strings representing the feature related to the examination position. In a case where the prior probability for the first probability and the prior probability for the second probability are 50%, and a certain number of character strings related to the left breast are extracted more than the number of the character strings related to the right breast, the voice analysis unit 24 can add a certain probability value to the prior probability for the first probability and subtract In this case, the voice analysis unit 24 can pick out the sentence related to the examination of the breast of the subject from among a plurality of sentences specified from the voice by using, for example, a so-called topic model such as a probabilistic latent semantic analysis (PLSA) as a trained model of so-called machine learning or deep learning. The voice analysis unit 24 can also pick out the sentence related to the examination of the breast of the subject by using a language model such as a recurrent neural network.

The voice analysis unit 24 calculates, for example, as shown in Table 2, the probabilities that the examination contents, "examination start", "left breast examination in progress", "right breast examination in progress", "examination switching from the left breast to the right breast", "examination switching from the right breast to the left breast", and "examination end", are currently being performed, based on the extracted specific character strings. The voice analysis unit 24 can calculate the probability of each examination content such that, for example, the probability is higher as the number of the related character strings is larger.

TABLE 2

| | Examination start | Left breast examination in progress | Right breast examination in progress | Examination switching from left breast to right breast | Examination switching from right breast to left breast | Examination end |
|---|---|---|---|---|---|---|
| Start examination | 95% | 1% | 1% | 1% | 1% | 1% |
| Start from left breast | 2% | 90% | 2% | 2% | 2% | 2% |
| Start examination of right breast now | 4% | 4% | 80% | 80% | 4% | 4% |
| Raise right hand | 2% | 2% | 90% | 2% | 2% | 2% |
| . . . | | | | | | |
| End examination | 1% | 1% | 1% | 1% | 1% | 95% |

For example, in a case where the sentence "start from the left breast" is specified from the voice, the character strings, "breast" and "left", are extracted. Therefore, the probability of the examination content, "left breast examination in progress", is calculated to be a relatively high value of 90%. In addition, for example, in a case where the sentence "start the examination of the right breast now" is specified from the voice, the character strings, "examination", "breast", "right", and "start", are extracted. Therefore, the probabilities of the examination contents, "right breast examination in progress" and "examination switching from the left breast to the right breast", related to these character strings are calculated to be a relatively high value of 80%.

For example, the voice analysis unit 24 can specify the left breast as the examination position in a case where the examination content, "left breast examination in progress", is equal to or greater than the probability threshold value, and can also specify the right breast as the examination position in a case where the examination content, "right breast examination in progress", is equal to or greater than the probability threshold value.

Additionally, ultrasound examinations may be generally performed in accordance with guidelines predetermined by associations, hospitals, or the like. The voice analysis unit 24 stores in advance, for example, a plurality of character strings following a predetermined guideline regarding the ultrasound examination of the breast of the subject, and can increase, in a case where voice data including dialogue between the subject and the examiner following the guideline is acquired by the voice acquisition sensor 3, a weight of the calculation of the first probability and the second probability based on the voice data.

For example, in a case where a guideline, "raise the upper arm up to the head in case of large breasts", is stored, and a sentence, "raise the right hand", is specified from the voice, the voice analysis unit 24 can increase a weight of the calculation of the second probability, such as setting the second probability that the examination position is the right breast to 90%.

As a result, the first probability and the second probability can be more accurately calculated in the ultrasound examination of the breast performed in accordance with the guideline.

In addition, a specific examination sequence for the ultrasound examination of the left and right breasts may be generally predetermined in hospitals or the like. The voice analysis unit 24 stores in advance, for example, a specific examination sequence for the ultrasound examination of the left and right breasts, and can calculate the first probability and the second probability based on respective prior probabilities by setting the prior probability for the first probability and the prior probability for the second probability based on the stored examination sequence. For example, in a case where an examination sequence in which the examination of the right breast is performed after the examination of the left breast is stored, and neither the examination of the left breast nor that of the right breast has been performed yet, the voice analysis unit 24 sets the prior probability for the first probability that the examination position is the left breast to be higher than the prior probability for the second probability. In addition, for example, in a case where an examination sequence in which the examination of the right breast is performed after the examination of the left breast is stored, and only the examination of the left breast has been completed, the voice analysis unit 24 sets the prior probability for the second probability that the examination position is the right breast to be higher than the prior probability for the first probability.

As a result, the first probability and the second probability can be more accurately calculated in the ultrasound examination of the breast performed in accordance with the specific examination sequence.

Figure 4:
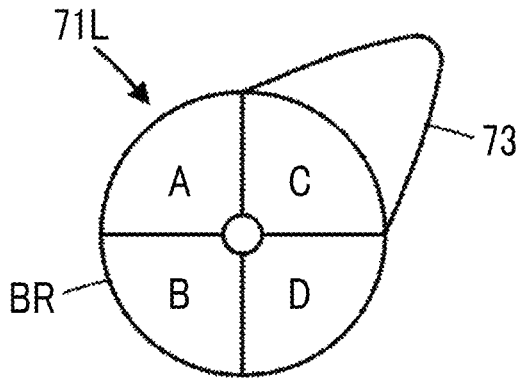
FIG. 4 is a diagram showing an example of a breast body mark representing a left breast in the embodiment of the present invention.
Figure 5:
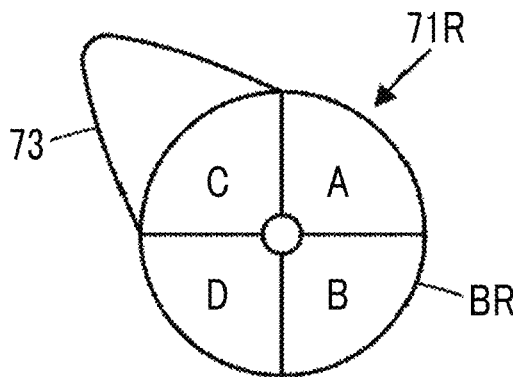
FIG. 5 is a diagram showing an example of a breast body mark representing a right breast in the embodiment of the present invention.

The body mark setting unit 25 selects and sets one of the left and right breast body marks based on the examination position of the subject estimated by the voice analysis unit 24. In addition, the body mark setting unit 25 can also set the breast body mark designated by the examiner via the input device 30. As the breast body mark, a breast body mark 71L imitating the left breast of the subject as shown in FIG. 4 and a breast body mark 71R imitating the right breast of the subject as shown in FIG. 5 are generally known.

The breast body mark 71L schematically indicates the left breast as viewed from the front and has a circular breast region BR and a substantially triangular axillary region 73 representing the axilla and extending diagonally upward from the breast region BR. The breast region BR is divided into four regions, that is, an inner upper region A, an inner lower region B, an outer upper region C, and an outer lower region D of the breast, and the axillary region 73 is connected to a left diagonal upper part of the outer upper region C.

The breast body mark 71R schematically indicates the right breast as viewed from the front and is obtained by horizontally reversing the breast body mark 71L indicating the left breast.

The breast body marks 71L and 71R set by the body mark setting unit 25 are sent to the image memory 26 and the notification unit 31.

The image memory 26, under the control of the control unit 29, stores the ultrasound image generated by the image generation unit 21 and the breast body marks 71L and 71R set by the body mark setting unit 25 in association with each other.

As the image memory 26, for example, recording media such as a flash memory, a hard disk drive (HDD), a solid state drive (SSD), a flexible disk (FD), a magneto-optical disk (MO disk), a magnetic tape (MT), a random access memory (RAM), a compact disc (CD), a digital versatile disc (DVD), a secure digital card (SD card), or a universal serial bus memory (USB memory), and the like can be used.

The measurement unit 27, under the control of the control unit 29, reads out the ultrasound image stored in the image memory 26 and performs the measurement of the subject at the examination position corresponding to the ultrasound image based on the read-out ultrasound image. The measurement unit 27 can measure, for example, dimensions or the like of anatomical structures in the breast appearing in the ultrasound image based on an input operation by the examiner via the input device 30.

The measurement result memory 28, under the control of the control unit 29, stores a result measured by the measurement unit 27 in association with the ultrasound image used for the measurement. As the measurement result memory 28, for example, recording media such as a flash memory, an HDD, an SSD, an FD, an MO disk, an MT, a RAM, a CD, a DVD, an SD card, or a USB memory, and the like can be used.

The input device 30 accepts the input operation by the examiner and sends input information to the control unit 29. The input device 30 is composed of, for example, a device for the examiner to perform an input operation such as a keyboard, a mouse, a trackball, a touchpad, or a touch panel.

The notification unit 31 issues a notification to the examiner. In particular, in a case where the breast body marks 71L and 71R automatically set by the body mark setting unit 25 based on the examination positions estimated by the voice analysis unit 24 are different from the body marks input by the examiner via the input device 30, the notification unit 31 issues a notification of an error to the examiner by displaying a message on the monitor 23 or the like.

Although the processor 43 including the image generation unit 21, the display control unit 22, the voice analysis unit 24, the body mark setting unit 25, the measurement unit 27, the control unit 29, and the notification unit 31 of the apparatus body 2 is configured with a central processing unit (CPU) and a control program for causing the CPU to perform various types of processing, the processor 43 may be configured by using a field programmable gate array (FPGA), a digital signal processor (DSP), an application specific integrated circuit (ASIC), a graphics processing unit (GPU), or other integrated circuits (ICs), or may be configured with a combination thereof.

In addition, the image generation unit 21, the display control unit 22, the voice analysis unit 24, the body mark setting unit 25, the measurement unit 27, the control unit 29, and the notification unit 31 of the processor 43 can also be configured by being integrated partially or entirely into one CPU or the like.

Next, an example of the operation of the ultrasound diagnostic apparatus according to the embodiment will be described by using the flowchart of FIG. 6.

First, in step S1, the breast body mark 71L or 71R is automatically set based on the voice during the examination. The processing of step S1 is composed of the processing of steps S11 to S14, as shown in the flowchart of FIG. 7.

In step S11, the voice acquisition sensor 3 acquires the voice including the conversation between the examiner and the subject during the examination.

In step S12, the voice analysis unit 24 calculates the first probability that the current examination position is the left breast and the second probability that the current examination position is the right breast by analyzing the voice during the examination acquired by the voice acquisition sensor 3 in step S11. Step S12 is composed of steps S21 to S23 as shown in the flowchart of FIG. 8.

In step S21, the voice analysis unit 24 converts the voice acquired in step S11 into a character string. In this case, the voice analysis unit 24 can use, for example, known statistical methods such as a method described in US2002/0059069A or a method as described in "Frederick Jelinek (1998), "Statistical Methods for Speech Recognition", MIT Press, ISBN 0-262-10066-5".

In step S22, the voice analysis unit 24 extracts a specific character string representing the feature related to the examination position from the character string obtained in step S21. In this case, the voice analysis unit 24 stores in advance, for example, a plurality of character strings related to the examination of the right breast and a plurality of character strings related to the examination of the left breast and can extract a specific character string by comparing these character strings stored in advance and the character string obtained by converting the voice with each other through pattern matching or the like.

In step S23, the voice analysis unit 24 calculates the first probability that the examination position is the left breast and the second probability that the examination position is the right breast based on the specific character string extracted in step S22. The voice analysis unit 24 stores in advance, for example, the prior probability for the first probability and the prior probability for the second probability and performs weighting on the first probability and the second probability based on the number of extracted character strings representing the feature related to the examination position. The voice analysis unit 24 can perform, for example, in a case where a certain number of character strings related to the left breast are extracted more than the number of the character strings related to the right breast, weighting on the respective prior probabilities such that the first probability is increased and the second probability is decreased. In addition, the voice analysis unit 24 can perform, for example, in a case where a certain number of character strings related to the right breast are extracted more than the number of the character strings related to the left breast, weighting on the respective prior probabilities such that the second probability is increased and the first probability is decreased.

By performing the processing of steps S21 to S23 in such a manner, the processing of step S12 is completed.

In subsequent step S13, the voice analysis unit 24 estimates whether the examination position is the left breast or the right breast based on the first probability and the second probability calculated in step S12. The voice analysis unit 24 has a predetermined probability threshold value, and for example, can specify the left breast as the examination position in a case where the first probability is equal to or greater than the probability threshold value and specify the right breast as the examination position in a case where the second probability is equal to or greater than the probability threshold value.

In step S14, the body mark setting unit 25 sets one of the left and right breast body marks 71L and 71R based on the examination position estimated in step S13.

In such a manner, in step S1, the breast body mark 71L or 71R is automatically and accurately set based on the voice during the ultrasound examination. In addition, it is not necessary to have an expensive and complicated apparatus configuration in order to estimate the examination position. Therefore, for example, despite an inexpensive and simple apparatus configuration, there is no need for the examiner to manually set the breast body mark 71L or 71R, and it is possible to prevent the examiner from incorrectly setting the breast body mark 71L or 71R.

In a case where the processing of step S1 is completed in such a manner, the process proceeds to step S2.

In step S2, the control unit 29 determines whether or not the voice is acquired by the voice acquisition sensor 3. The control unit 29 can determine that the voice is acquired by the voice acquisition sensor 3 in a case where the voice analysis unit 24 receives the voice including the conversation between the examiner and the subject from the voice acquisition sensor 3, and can determine that the voice is not acquired by the voice acquisition sensor 3 in a case where the voice analysis unit 24 does not receive the voice including the conversation between the examiner and the subject from the voice acquisition sensor 3.

In a case where it is determined in step S2 that the voice is acquired by the voice acquisition sensor 3, the process proceeds to step S3. In step S3, the voice analysis unit 24 analyzes the voice acquired in step S2 in the same manner as in step S11 to convert the voice into a character string.

In step S4, the voice analysis unit 24 estimates the examination position based on the character string obtained in step S3 in the same manner as in step S12.

In step S5, the body mark setting unit 25 determines whether or not the examination position estimated in step S4 matches the current breast body mark 71L or 71R set in step S1. In a case where it is determined that the examination position estimated in step S4 corresponds to the current breast body mark 71L or 71R and matches the breast body mark 71L or 71R, the process proceeds to step S6.

In step S6, the breast of the subject is scanned by the ultrasound probe 1, and the ultrasound image representing a tomographic image of the breast is acquired. In this case, the transmission and reception circuit 12 performs so-called reception focus processing to generate the sound ray signal, under the control of the control unit 29. The sound ray signal generated by the transmission and reception circuit 12 is sent to the image generation unit 21. The image generation unit 21 generates the ultrasound image by using the sound ray signal sent from the transmission and reception circuit 12.

The ultrasound image acquired in such a manner is sent to the display control unit 22 and the image memory 26.

In step S7, the ultrasound image acquired in step S6 and the breast body mark 71L or 71R set in step S1 are displayed on the monitor 23. In addition, the ultrasound image acquired in step S6 and the breast body mark 71L or 71R set in step S1 are stored in the image memory 26 in association with each other.

In step S8, the control unit 29 determines whether or not to end the ultrasound examination. For example, in a case where instruction information to end the ultrasound examination is input by the examiner via the input device 30, the control unit 29 determines to end the current ultrasound examination. Alternatively, for example, in a case where no instruction information to end the ultrasound examination is input by the examiner via the input device 30, it is determined to continue the current examination.

In a case where it is determined in step S8 to continue the ultrasound examination, the process returns to step S2. Subsequently, the processing of steps S2 to S8 is repeated as long as it is determined in step S2 that the voice is acquired, it is determined in step S5 that the estimated examination position matches the current breast body mark 71L or 71R, and it is determined in step S8 to continue the examination. In the repetition of steps S2 to S8, the examiner continues the ultrasound examination while moving the ultrasound probe 1 on the subject.

In addition, in step S5, in a case where it is determined that the examination position estimated in step S4 does not match the breast body mark 71L or 71R set in step S1 because the examination location of the subject by the examiner is moved from one of the left or right breast to the opposite breast, the process proceeds to step S9.

In step S9, the body mark setting unit 25 changes the breast body mark 71L or 71R corresponding to the examination position estimated in step S4.

Consequently, the breast body mark 71L or 71R corresponding to the current examination position is correctly set.

In a case where the processing of step S9 is completed, the process proceeds to step S6.

In addition, in step S2, in a case where the control unit 29 determines that the voice acquisition sensor 3 has not acquired the voice, the processing of steps S3 to S5, and step S9 is skipped, and the process proceeds to step S6.

Figure 6:
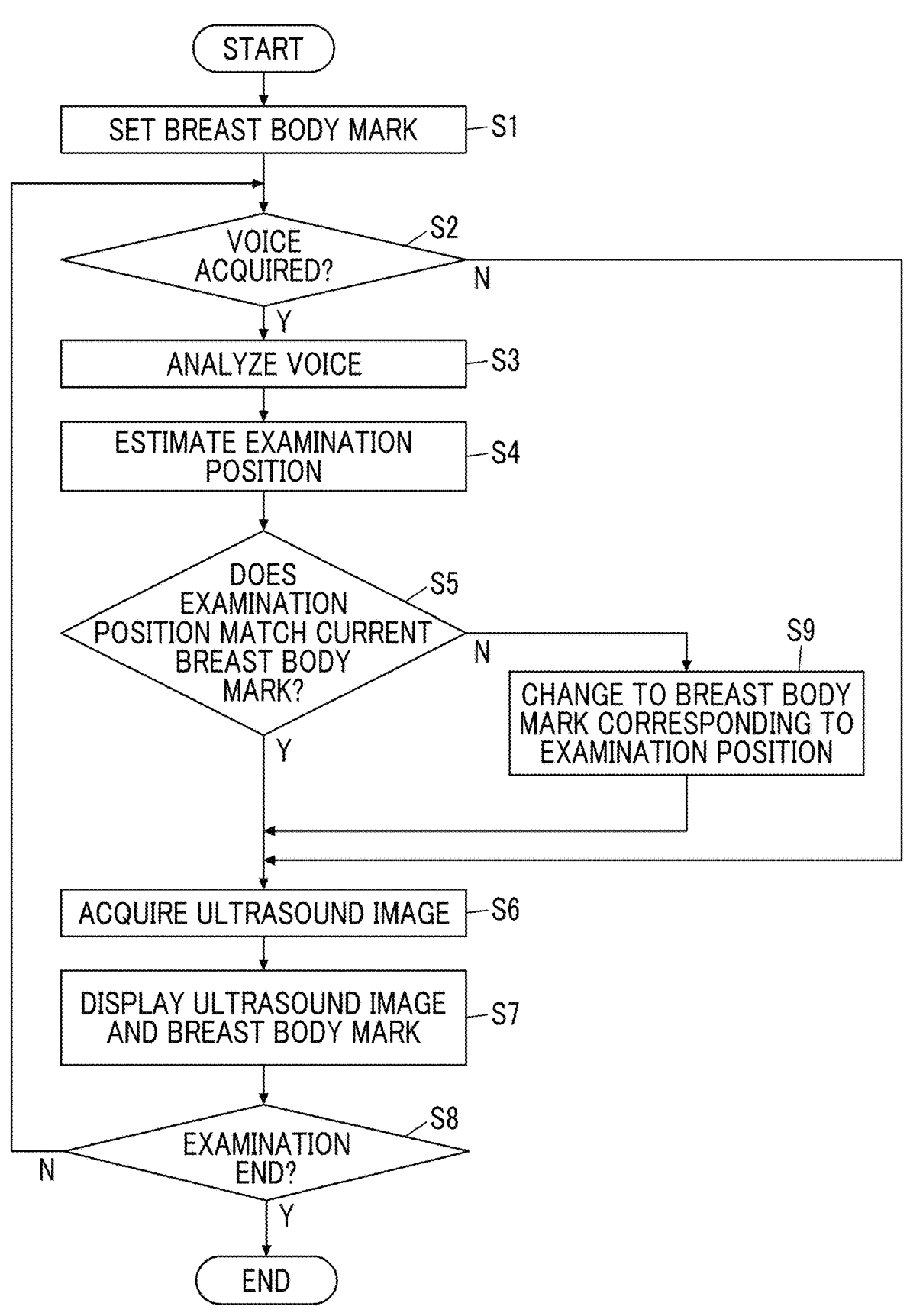
FIG. 6 is a flowchart showing an operation of the ultrasound diagnostic apparatus according to the embodiment of the present invention.

In step S8, in a case where it is determined to end the ultrasound examination by the control unit 29, the operation of the ultrasound diagnostic apparatus following the flowchart of FIG. 6 ends.

As described above, with the ultrasound diagnostic apparatus according to the embodiment of the present invention, the voice analysis unit 24 analyzes the voice during the ultrasound examination acquired by the voice acquisition sensor 3 to estimate whether the current examination position is either the left or right breast of the subject, and the body mark setting unit 25 automatically sets the breast body mark 71L or 71R based on the estimated examination position, so that the breast body mark 71L or 71R can be accurately set even with an inexpensive and simple apparatus configuration.

The image generation unit 21 has been described as being provided in the apparatus body 2, but the image generation unit 21 can also be provided in the ultrasound probe 1 instead of being provided in the apparatus body 2.

In addition, the voice acquisition sensor 3 has been described as being provided in the ultrasound diagnostic apparatus independently of the ultrasound probe 1 and the apparatus body 2, but the voice acquisition sensor 3 can be attached to the ultrasound probe 1 and can also be attached to the apparatus body 2. Further, the voice acquisition sensor 3 can also be attached to, for example, a so-called headphone and earphone worn by the examiner.

Additionally, the breast body mark 71L or 71R has been described as being automatically set in step S1, but, for example, the breast body mark 71L or 71R can also be manually input by the examiner by selecting the breast body mark 71L or 71R via the input device 30. In this case, in step S5, in a case where it is determined that the examination position estimated in step S4 does not match the breast body mark 71L or 71R manually input in step S1, the breast body mark 71L or 71R corresponding to the examination position estimated in step S4 is set in step S9. Therefore, even in a case where the breast body mark 71L or 71R is manually input in step S1, the breast body mark 71L or 71R is accurately set.

In addition, in the flowchart of FIG. 6, measurement processing by the measurement unit 27 can also be added. For example, in step S7, the ultrasound image and the breast body mark 71L or 71R are displayed on the monitor 23 and stored in the image memory 26, and then the measurement by the measurement unit 27 can be performed. In this case, the measurement unit 27 can read out the ultrasound image stored in step S7 from the image memory 26 and measure the dimensions or the like of the anatomical structures in the ultrasound image based on an input operation by the examiner via the input device 30. A measurement result obtained by the measurement unit 27 in such a manner is stored in the measurement result memory 28.

Figure 9:
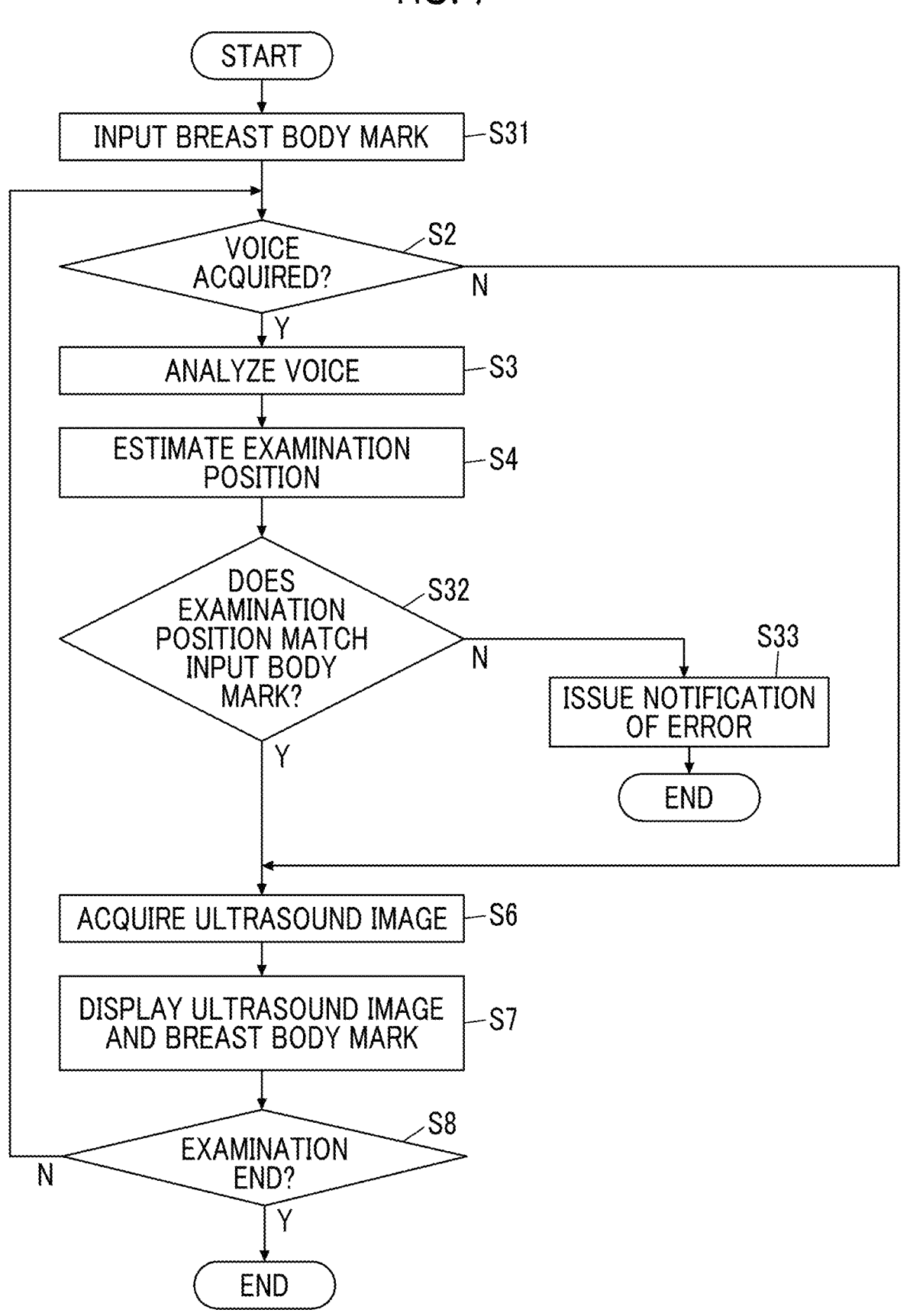
FIG. 9 is a flowchart showing an operation of the ultrasound diagnostic apparatus in a modification example of the embodiment of the present invention.

In addition, in a case where the breast body mark 71L or 71R is manually input by the examiner, and the estimated examination position does not match the set breast body mark 71L or 71R, a notification of an error can be issued to the examiner. This aspect will be described with reference to the flowchart of FIG. 9. The flowchart of FIG. 9 shows an operation in which, in the flowchart of FIG. 6, step S31 is performed instead of step S1, step S32 is performed instead of step S5, and step S33 is performed instead of step S9. Since steps S2 to S4 and steps S6 to S8 in the flowchart of FIG. 9 are the same as steps S2 to S4 and steps S6 to S8 in the flowchart of FIG. 6, the detailed descriptions of the processing will not be repeated.

First, in step S31, the breast body mark 71L or 71R is input by an input operation by the examiner via the input device 30.

In subsequent step S2, the control unit 29 determines whether or not the voice during the ultrasound examination is acquired by the voice acquisition sensor 3. In a case where it is determined in step S2 that the voice is acquired, the process proceeds to step S3.

In step S3, the voice analysis unit 24 analyzes the voice acquired in step S2 to calculate the first probability that the examination position is the left breast and the second probability that the examination position is the right breast.

In step S4, the voice analysis unit 24 estimates the current examination position based on the first probability and the second probability calculated in step S3.

In subsequent step S32, the control unit 29 determines whether or not the examination position estimated in step S4 matches the breast body mark 71L or 71R input by the examiner in step S31. In step S32, in a case where it is determined that the current examination position matches the breast body mark 71L or 71R input in step S31, the process proceeds to step S6, and in a case where it is determined that the current examination position does not match the breast body mark 71L or 71R, the process proceeds to step S33.

In step S33, the notification unit 31 issues a notification of an error to the examiner by displaying a message on the monitor 23 or the like. The examiner can re-set the breast body mark 71L or 71R that matches the current examination position by confirming the notification of the error. Consequently, the breast body mark 71L or 71R that matches the examination position can be accurately set.

In a case where the processing of step S33 is completed in such a manner, the operation of the ultrasound diagnostic apparatus following the flowchart of FIG. 9 ends.

Here, the notification unit 31 can also issue a notification of an error to the examiner by using a method other than displaying the message or the like on the monitor 23. For example, in a case where the ultrasound diagnostic apparatus comprises a speaker (not shown), the notification unit 31 can issue a notification of an error to the examiner by emitting a sound from the speaker. In addition, for example, in a case where the ultrasound diagnostic apparatus comprises a lamp (not shown), the notification unit 31 can issue a notification of an error to the examiner by turning on or blinking the lamp.

EXPLANATION OF REFERENCES

1: ultrasound probe
2: apparatus body
3: voice acquisition sensor
11: transducer array
12: transmission and reception circuit
21: image generation unit
22: display control unit
23: monitor
24: voice analysis unit
25: body mark setting unit
26: image memory
27: measurement unit
28: measurement result memory
29: control unit
30: input device
31: notification unit
41: image acquisition unit
43: processor
51: pulsar
52: amplification section
53: AD conversion section
54: beam former
55: signal processing section
56: DSC
57: image processing section
71L, 71R: breast body mark
73: axillary region
A: inner upper region
B: inner lower region
C: outer upper region
D: outer lower region

What is claimed is:

1. An ultrasound diagnostic apparatus for an examiner to perform an ultrasound examination on a breast of a subject, the ultrasound diagnostic apparatus comprising:
   a voice acquisition sensing device configured to acquire a voice during the ultrasound examination;
   a processor configured to:
      extract a feature related to an examination position of the subject from the voice acquired by the voice acquisition sensing device;
      calculate a first probability that the examination position is a left breast and a second probability that the examination position is a right breast, based on the feature;
      estimate the examination position based on the first probability and the second probability; and
      select and set one of left and right breast body marks based on the examination position of the subject which is estimated.

2. The ultrasound diagnostic apparatus according to claim 1, wherein the processor is configured to extract the feature from the voice representing a series of operation transitions of the ultrasound examination.

3. The ultrasound diagnostic apparatus according to claim 2, wherein the processor is configured to accept input of any of the left and right breast body marks through an input operation by the examiner prior to the ultrasound examination.

4. The ultrasound diagnostic apparatus according to claim 2, wherein the processor is configured to:

convert the voice acquired by the voice acquisition sensing device into a character string; and extract a feature related to the examination position from the converted character string.

5. The ultrasound diagnostic apparatus according to claim 2, further comprising:

a monitor; and an ultrasound probe, wherein the processor is configured to:

acquire an ultrasound image in the breast of the subject by performing transmission and reception of an ultrasound beam using the ultrasound probe; and display the ultrasound image on the monitor.

6. The ultrasound diagnostic apparatus according to claim 1, wherein the processor is configured to accept input of any of the left and right breast body marks through an input operation by the examiner prior to the ultrasound examination.

7. The ultrasound diagnostic apparatus according to claim 6, wherein the processor is configured to:

issue a notification to the examiner; and upon that the breast body mark selected based on the examination position of the subject is different from the breast body mark input by the examiner, issue a notification of an error.

8. The ultrasound diagnostic apparatus according to claim 7, wherein the processor is configured to:

convert the voice acquired by the voice acquisition sensing device into a character string; and extract a feature related to the examination position from the converted character string.

9. The ultrasound diagnostic apparatus according to claim 7, further comprising:

a monitor; and an ultrasound probe, wherein the processor is configured to:

acquire an ultrasound image in the breast of the subject by performing transmission and reception of an ultrasound beam using the ultrasound probe; and display the ultrasound image on the monitor.

10. The ultrasound diagnostic apparatus according to claim 6, wherein the processor is configured to:

upon that the breast body mark selected based on the examination position of the subject is different from the breast body mark input by the examiner, set the breast body mark selected based on the examination position of the subject, instead of the breast body mark input by the examiner.

11. The ultrasound diagnostic apparatus according to claim 10, wherein the processor is configured to:

convert the voice acquired by the voice acquisition sensing device into a character string; and extract a feature related to the examination position from the converted character string.

12. The ultrasound diagnostic apparatus according to claim 6, wherein the processor is configured to:

convert the voice acquired by the voice acquisition sensing device into a character string; and extract a feature related to the examination position from the converted character string.

13. The ultrasound diagnostic apparatus according to claim 6, further comprising:

a monitor; and an ultrasound probe, wherein the processor is configured to:

acquire an ultrasound image in the breast of the subject by performing transmission and reception of an ultrasound beam using the ultrasound probe; and display the ultrasound image on the monitor.

14. The ultrasound diagnostic apparatus according to claim 1, wherein the processor is configured to:

convert the voice acquired by the voice acquisition sensing device into a character string; and extract a feature related to the examination position from the converted character string.

15. The ultrasound diagnostic apparatus according to claim 1, further comprising:

a monitor; and an ultrasound probe, wherein the processor is configured to:

acquire an ultrasound image in the breast of the subject by performing transmission and reception of an ultrasound beam using the ultrasound probe; and display the ultrasound image on the monitor.

16. The ultrasound diagnostic apparatus according to claim 15, wherein the processor is configured to display the breast body mark selected based on the examination position of the subject on the monitor together with the ultrasound image.

17. The ultrasound diagnostic apparatus according to claim 1, wherein the processor is configured to:

store a specific examination sequence for an ultrasound examination of the left and right breasts; and calculate the first probability and the second probability based on respective prior probabilities corresponding to the specific examination sequence.

18. The ultrasound diagnostic apparatus according to claim 17, wherein the voice acquisition sensing device is configured to acquire voice data including dialogue between the subject and the examiner following a predetermined guideline, and the processor is configured to increase a weight of the calculation of the first probability or the second probability based on the voice data.

19. The ultrasound diagnostic apparatus according to claim 1, wherein the voice acquisition sensing device is configured to acquire voice data including dialogue between the subject and the examiner following a predetermined guideline, and the processor is configured to increase a weight of the calculation of the first probability or the second probability based on the voice data.

20. A control method of an ultrasound diagnostic apparatus for an examiner to perform an ultrasound examination on a breast of a subject, the control method comprising:

acquiring a voice during the ultrasound examination;

extracting a feature related to an examination position of the subject from the voice;

calculating a first probability that the examination position is a left breast and a second probability that the examination position is a right breast, based on the feature;

estimating the examination position based on the first probability and the second probability; and selecting and setting one of left and right breast body marks based on the estimated examination position of the subject.

* * * * *